(12) United States Patent
Bambot et al.

(10) Patent No.: US 6,590,651 B1
(45) Date of Patent: Jul. 8, 2003

(54) APPARATUS AND METHOD FOR DETERMINING TISSUE CHARACTERISTICS

(75) Inventors: Shabbir Bambot, Suwanne, GA (US); Mark L. Faupel, Alphretta, GA (US); Glenn Steven Arche, Duluth, GA (US)

(73) Assignee: SpectRx, Inc., Norcross, GA (US)

( * ) Notice: Subject to any disclaimer, the term of this patent is extended or adjusted under 35 U.S.C. 154(b) by 0 days.

(21) Appl. No.: 09/700,538

(22) PCT Filed: May 19, 1999

(86) PCT No.: PCT/US99/10947

§ 371 (c)(1),
(2), (4) Date: Nov. 16, 2000

(87) PCT Pub. No.: WO99/60377

PCT Pub. Date: Nov. 25, 1999

Related U.S. Application Data

(60) Provisional application No. 60/085,941, filed on May 19, 1998.

(51) Int. Cl.$^7$ .............................. G01N 21/00; A61B 1/06
(52) U.S. Cl. ........................................ 356/338; 600/182
(58) Field of Search .................... 356/39, 337, 338; 600/137, 138, 160, 182

(56) References Cited

U.S. PATENT DOCUMENTS

| 4,213,462 A | * | 7/1980 | Sato ........................... 128/634 |
|---|---|---|---|
| 5,192,278 A | | 3/1993 | Hayes et al. |
| 5,797,836 A | | 8/1998 | Lucey et al. |
| 5,916,210 A | | 6/1999 | Winston |

\* cited by examiner

*Primary Examiner*—Michael P. Stafira
(74) *Attorney, Agent, or Firm*—Fleshner & Kim, LLP

(57) ABSTRACT

An apparatus and method embodying the invention include utilizing a device with a limited number of interrogation devices to accomplish a large number of measurements on a target tissue (50). An instrument embodying the invention includes a plurality of detection devices (54) that are arranged in a predetermined pattern on a tissue contacting face of the instrument. The face of the instrument is located adjacent the target tissue (50), and a plurality of tissue characteristic measurement are simultaneously conducted. The detection devices (54) are moved to a new position, preferably without moving the tissue contacting face, and a second plurality of tissue characteristic measurements are simultaneously conducted. By conducting a series of measurements cycles in this manner, the ultimate resolution of the device is increased, while still obtaining a given resolution, which reduces potential cross-talk errors. Further, a plurality of tissue characteristics are simultaneously obtained from locations spaced across the target tissue (50) during each measurement cycle.

21 Claims, 12 Drawing Sheets

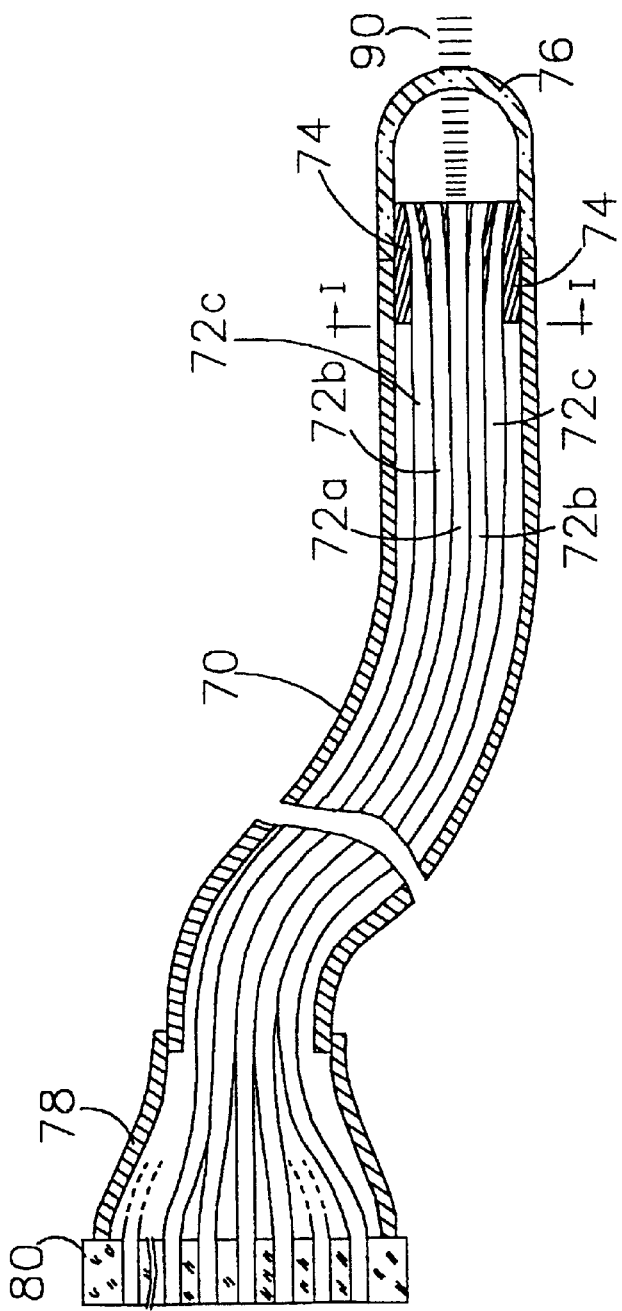
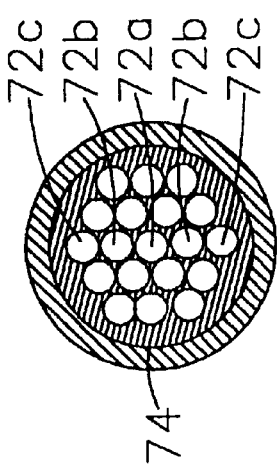
FIG. 5A
FIG. 5B

APPARATUS AND METHOD FOR DETERMINING TISSUE CHARACTERISTICS

This application claims the benefit of Ser. No. 60/085,941, filed May 19, 1998.

BACKGROUND OF THE INVENTION

1. Field of the Invention

The invention is related to apparatus and methods for determining tissue characteristics within a body of a patient.

2. Background of the Related Art

It is known to irradiate a target tissue with electromagnetic radiation and to detect returned electromagnetic radiation to determine characteristics of the target tissue. In known methods, the amplitudes and wavelengths of the returned radiation are analyzed to determine characteristics of the target tissue. For instance, U.S. Pat. No. 4,718,417 to Kittrell et al. discloses a method for diagnosing the type of tissue within an artery, wherein a catheter is inserted into an artery and excitation light at particular wavelengths is used to illuminate the interior wall of the artery. Material or tissue within the artery wall emits fluorescent radiation in response to the excitation light. A detector detects the fluorescent radiation and analyzes the amplitudes and wavelengths of the emitted fluorescent radiation to determine whether the illuminated portion of the artery wall is normal, or covered with plaque. The contents of U.S. Pat. No. 4,718,417 are hereby incorporated by reference.

U.S. Pat. No. 4,930,516 to Alfano et al. discloses a method for detecting cancerous tissue, wherein a tissue sample is illuminated with excitation light at a first wavelength, and fluorescent radiation emitted in response to the excitation light is detected. The wavelength and amplitude of the emitted fluorescent radiation are then examined to determine whether the tissue sample is cancerous or normal. Normal tissue will typically have amplitude peaks at certain known wavelengths, whereas cancerous tissue will have amplitude peaks at different wavelengths. Alternatively the spectral amplitude of normal tissue will differ from cancerous tissue at the same wavelength. The disclosure of U.S. Pat. No. 4,930,516 is hereby incorporated by reference.

Still other patents, such as U.S. Pat. No. 5,369,496 to Alfano et al., disclose methods for determining characteristics of biological materials, wherein a target tissue is illuminated with light, and backscattered or reflected light is analyzed to determine the tissue characteristics. The contents of U.S. Pat. No. 5,369,496 are hereby incorporated by reference.

These methods rely on the information from steady state emissions to perform a diagnostic measurement. It is known that the accuracy of measurements made by these methods is limited by practical issues such as variation in lamp intensity and changes in fluorophore concentration. It is desirable to measure an intrinsic physical property to eliminate errors that can be caused by practical problems, to thereby make an absolute measurement with greater accuracy. One intrinsic physical property is the fluorescence lifetime or decay time of fluorophores being interrogated, the same fluorophores that serve as indicators of disease in tissue.

It is known to look at the decay time of fluorescent emissions to determine the type or condition of an illuminated tissue.

To date, apparatus for detection of the lifetime of fluorescent emissions have concentrated on directly measuring the lifetime of the fluorescent emissions. Typically, a very short burst of excitation light is directed at a target tissue, and fluorescent emissions from the target tissue are then sensed with a detector. The amplitude of the fluorescent emissions are recorded, over time, as the fluorescent emissions decay. The fluorescent emissions may be sensed at specific wavelengths, or over a range of wavelengths. The amplitude decay profile, as a function of time, is then examined to determine a property or condition of the target tissue.

For instance, U.S. Pat. No. 5,562,100 to Kittrell et al. discloses a method of determining tissue characteristics that includes illuminating a target tissue with a short pulse of excitation radiation at a particular wavelength, and detecting fluorescent radiation emitted by the target tissue in response to the excitation radiation. In this method, the amplitude of the emitted radiation is recorded, over time, as the emission decays. The amplitude profile is then used to determine characteristics of the target tissue. Similarly, U.S. Pat. No. 5,467,767 to Alfano et al. also discloses a method of determining whether a tissue sample includes cancerous cells, wherein the amplitude decay profile of fluorescent emissions are examined. The contents of U.S. Pat. Nos. 5,562,100 and 5,467,767 are hereby incorporated by reference.

Unfortunately, these methods require expensive components that are capable of generating extremely short bursts of excitation light, and that are capable of recording the relatively faint fluorescent emissions that occur over time. The high cost of these components has prevented these techniques from being used in typical clinical settings. Other U.S. patents have explained that the decay time of fluorescent emissions can be indirectly measured utilizing phase shift or polar anisotropy measurements. For instance, U.S. Pat. No. 5,624,847 to Lakowicz et al. discloses a method for determining the presence or concentration of various substances using a phase shift method. U.S. Pat. No. 5,515,864 to Zuckerman discloses a method for measuring the concentration of oxygen in blood utilizing a polar anisotropy measurement technique. Each of these methods indirectly measure the lifetime of fluorescent emissions generated in response to excitation radiation. The contents of U.S. Pat. Nos. 5,624,847 and 5,515,864 are hereby incorporated by reference.

SUMMARY OF THE INVENTION

The invention encompasses apparatus and methods for determining characteristics of target tissues within or at the surface of a patient's body, wherein excitation electromagnetic radiation is used to illuminate a target tissue and electromagnetic radiation returned from the target tissue is analyzed to determine the characteristics of the target tissue. Some apparatus and methods embodying the invention can be used to perform a diagnosis at or slightly below the surface of a patient=s tissues. For instance, methods and apparatus embodying the invention could be used to diagnose the condition of a patient=s skin, the lining of natural body lumens such as the gastrointestinal tract, or the surfaces of body organs or blood vessels. Embodiments of the invention are particularly well suited to analyzing epithelial tissue. Other apparatus and methods embodying the invention can be used to perform a diagnosis deep within a patient=s body tissues where the excitation radiation has to pass through several centimeters of tissue before it interacts with the target tissue, such as in diagnosis of tumors and lesions deep in a patient=s breast.

The returned electromagnetic radiation can comprise only fluorescent emissions from the target tissue that are caused by the excitation electromagnetic radiation. In this instance, apparatus or methods embodying the invention would measure the lifetime or decay time of the fluorescent emissions and use this information to determine characteristics of the target tissue. The fluorescent emissions may be generated by endogenous or exogenous fluorescent materials in the target tissue. Both phase shift and polar anisotropy techniques can be used to perform these types of measurements.

The returned electromagnetic radiation can also comprise a portion of the electromagnetic radiation that is scattered or reflected from or transmitted through the target tissue. Analysis of the scattered, reflected or transmitted excitation radiation gives a measure of absorption and scattering characteristics of the target tissue. This information can be used by itself to provide a diagnosis, or the information can be used to calibrate the results of the fluorescent emission measurements to arrive at a more accurate measurement. The reflected or scattered excitation radiation can be measured using intensity based techniques, or phase shift techniques.

In phase shift techniques for measuring either reflected or scattered excitation radiation, or fluorescent emissions caused by the excitation radiation, the excitation electromagnetic radiation is amplitude modulated at a predetermined frequency. A detector that senses the returned radiation (either reflected/scattered excitation radiation or fluorescent emissions) is used to detect the amplitude and timing characteristics of the returned electromagnetic radiation. The excitation and returned radiation will have the same frequency, but the amplitude of the returned radiation should be smaller than the amplitude of the excitation radiation, and the returned radiation will be out of phase with the excitation radiation. The demodulation and phase shift between the excitation and returned electromagnetic radiation gives a measure of the characteristics of the target tissue. The demodulation amount can be represented by a demodulation factor, which is a ratio of the AC and DC amplitude components of the excitation and returned electromagnetic radiation.

A polar anisotropy technique may also be used to detect fluorescent emissions to obtain a measure of the decay time or lifetime of the fluorescent emissions. In the polar anisotropy techniques, the target tissue is illuminated with polarized excitation electromagnetic radiation. The returned fluorescent emissions are conveyed to a polarizing beam splitter that separates the returned electromagnetic radiation into two light beams that are polarized in mutually perpendicular planes. In a preferred embodiment, one plane is parallel to the polarization plane of the excitation radiation, and the second plane is perpendicular to that plane. Detectors detect the amplitudes of the two perpendicularly polarized beams of light. The detected amplitudes are used to calculate an anisotropy factor that is representative of the lifetime or decay time of the fluorescent emissions.

In either the phase shift or polar anisotropy techniques, the apparatus or method may only analyze returned radiation within certain predetermined wavelengths. Also, the apparatus and methods may only analyze fluorescent decays that occur for more than a predetermined period of time, or less than a predetermined period of time. This allows the device to distinguish between different types of tissues that have different fluorescent decay times.

Because of changes in the fluorescent emissions of endogenous and exogenous fluorophores that occur within a patient=s body, the above-described methods were not previously used for in vivo detection of cancerous or diseased tissues. Methods and apparatus embodying the present invention, however, allow for in vivo detection of diseased tissues using relatively simple and inexpensive instrumentation.

The above described techniques can be used to determine the conditions of multiple portions of a target tissue, and the determined conditions can be used to create a map of the target tissue. Such a map could then be either displayed on a display screen, or presented in hard copy format.

An instrument embodying present invention could be in the form of an endoscope designed to be introduced into natural lumen or a cavity of a patient=s body. Alternatively, the instrument might be in the form of a catheter designed to be introduced into blood vessels of a patient=s body. Regardless of whether the apparatus is in the form of an endoscope or a catheter, the apparatus could include means for delivering a therapeutic pulse of electromagnetic radiation to the target tissue. The device could also include means for delivering a therapeutic dose of medication to the target tissue. Further, the instrument could include means for sampling the target tissue depending upon the determined condition of the target tissue.

An apparatus embodying the invention that is well suited to developing a map of target tissue conditions may include a plurality of optical fibers that are arranged in a predetermined pattern on the face of a test instrument. Each optical fiber would be capable of delivering excitation radiation and conducting return radiation to a detector. Alternatively, each detection position on the face of the instrument could include one optical fiber for delivering excitation radiation and another fiber for receiving returned radiation. In yet other alternatives, multiple fibers could be used at each position for the excitation or return radiation, or both. By pressing the face of the instrument against the target tissue, multiple measurements can be taken at multiple positions simultaneously.

An apparatus as described above could also be configured so that once a first set of measurements are taken with the instrument, the locations of the optical fibers could be moved incrementally, and a second set of measurements could be recorded. This could be done by repositioning the instrument face, or by keeping the instrument face stationary, and repositioning the optical fibers behind the instrument face. This process could be repeated several times to obtain multiple sets of readings from the target tissue. The additional sets of measurements could be taken on the same area as the first set, or at different locations on the target tissue.

An instrument as described above could be configured to allow rotation of the optical fibers between a plurality of predetermined rotational positions. One embodiment could be configured so that the optical fibers are located at a series of unique positions as the optical fibers are rotated between the predetermined rotational positions. This would allow the device to capture multiple readings at a large number of unique positions on the target tissue. Such a multiple cycle measurement process would allow greater resolution than would be possible with a single measurement cycle.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

Preferred embodiments of the present invention will now be described with reference to the following drawing figures, wherein like elements are referred to with like reference numerals, and wherein:

FIGS. 5A and 5B show an embodiment of the invention;

DETAILED DESCRIPTION OF PREFERRED EMBODIMENTS

The phase shift and polar anisotropy techniques that can be used in devices embodying the invention are more simple and less expensive to implement than the known apparatus and techniques for detecting the lifetime or decay time of fluorescent emissions. As a result, they can be implemented for real world in vivo testing of target tissues.

It is known that when a fluorophore is excited with an infinitesimal pulse of light, the resulting fluorescent emission decays exponentially. The intensity of the fluorescent emission is given by Equation (1), where $I_i$ is the initial fluorescence intensity, t is the time, and t is the fluorescence lifetime.

$$I(t)=I_i e^{-t/t} \qquad \text{Equation (1)}$$

If an excitation light is amplitude modulated at a constant frequency, instead of simply illuminating the target tissue with a short burst of light, the resulting fluorescence emissions will also appear to be amplitude modulated. The amplitude of the fluorescent emissions will be smaller than the amplitude of the excitation light, but the fluorescent emissions will have the same frequency. Also, there will be a phase shift between the excitation light and the fluorescent emissions.

Figure 1:
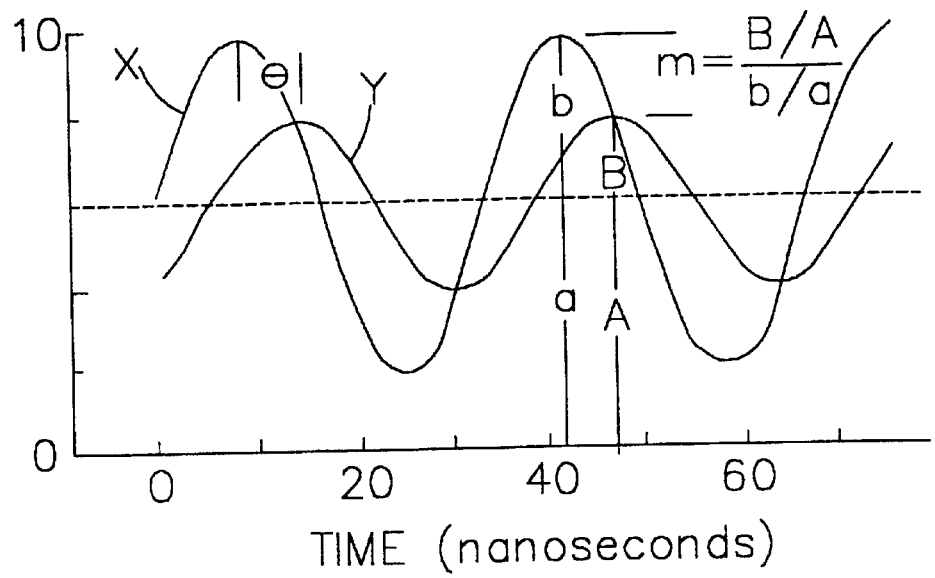
FIG. 1 is a chart showing the amplitudes and phase shift of excitation and returned electromagnetic radiation.

FIG. 1 illustrates the concept of illuminating a target tissue with amplitude modulated excitation electromagnetic radiation and sensing the resulting fluorescent emissions. In FIG. 1, the waveform X shows the amplitude of modulated excitation electromagnetic radiation from a source. The amplitude of returned fluorescent emissions is shown as waveform Y. As can be seen in FIG. 1, the peaks of the waveform Y are delayed, or phase shifted, relative to the peaks of waveform X by an amount q. This is referred to as a phase shift amount.

In addition, the amplitude of the fluorescent emissions is smaller than the amplitude of the excitation light source. A demodulation factor m represents a ratio of the DC and AC components of the fluorescent emissions relative to the DC and AC components of the excitation electromagnetic radiation.

The Fourier transform of equation (1), yields Equation (2), shown below.

$$I(w)=I_i t/(1--iwt) \qquad \text{Equation (2)}$$

Equation (2), in turn, can be used to derive the phase shift and demodulation factor, as shown in Equations (3) and (4) below.

$$q_s=\tan^{-1}(wt) \qquad \text{Equation (3)}$$

$$m=1/\%(1+w^2 t^2) \qquad \text{Equation (4)}$$

An apparatus for in vivo determination of the characteristics of a target tissue utilizing a phase shift technique will now be described with reference to FIGS. 1 and 2.

Figure 2:
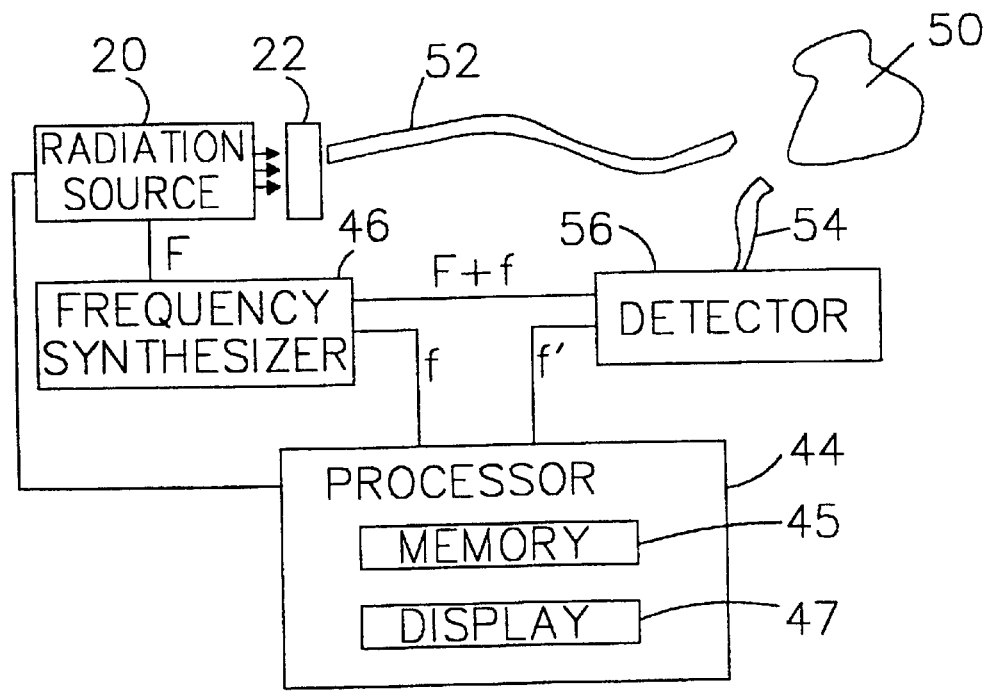
FIG. 2 is a diagram showing an apparatus embodying the invention capable of performing a phase shift measurement.

A diagram of an apparatus embodying the invention is shown in FIG. 2. The apparatus includes a source 20 of electromagnetic radiation, which is connected to a frequency synthesizer 46. The radiation source 20 produces electromagnetic radiation that is conducted to a target tissue 50. The radiation may be conducted to the target tissue 50 through one or more emission optical fibers 52. The apparatus may also include a filter 22 for controlling the electromagnetic radiation emitted from the radiation source 20. The radiation source could comprise a laser, a light emitting diode, a fluorescent tube, an incandescent bulb, or any other type of device that is capable of emitting electromagnetic radiation, as is well known to those skilled in the art.

Electromagnetic radiation returned from target tissue 50, is sensed by a detector 56. The returned electromagnetic radiation could comprise either a portion of the excitation electromagnetic radiation that is scattered or reflected from the target tissue, or fluorescent emissions from fluorophores in the target tissue that have been excited by the excitation radiation. The detector may comprise a photomultiplier tube, a photosensitive diode, a charge coupled device, or any other type of electromagnetic radiation sensor, as is also well known to those skilled in the art.

If the detector is a small charge coupled device, it could be located at a distal end of an endoscope or catheter instrument. In this instance, the charge coupled device would already be located adjacent the target tissue such that the detector could directly sense the return radiation. The charge coupled device would then need some means for communicating its information to a processor 44.

If the detector is not a charge coupled device located at a distal end of an instrument, the returned electromagnetic radiation may be conducted to the detector 56 through one or more return optical fibers 54. The return optical fibers 54 and the excitation optical fibers 52 may be co-located within the same instrument, or they may be located in separate instruments. Alternately, the same optical fibers within an instrument may be used to perform both excitation and return functions.

The frequency synthesizer 46 is a combination of two high frequency synthesizers that are preferably phase locked. The frequency synthesizer outputs three signals. The first signal has a frequency F, the second signal has a frequency of F+f, which is a slightly in frequency than the signal F, and the third signal has a frequency f, which is lower in frequency than the first two signals.. The excitation radiation from the radiation source 20, which illuminates the target tissue 50, is amplitude modulated at the high frequency F. The signal F+f drives the detector 56. Finally, the low frequency signal f, which is readily derived as the difference between the two high frequency signals, is sent as a reference signal to the processor 44.

The embodiment shown in FIG. 2, is a heterodyne system. The detector 56 senses the returned radiation and generates a signal that is modulated at the same frequency as the excitation radiation, or the frequency F. The detector 56 then uses the higher frequency signal F+f to convert the signal corresponding to the returned radiation into a low difference frequency signal f=, which includes information on the returned radiation signal. The low frequency signal f= is then compared to the low frequency signal f, which was generated by the frequency synthesizer 46, to calculate a phase shift q and demodulation factor m. Other types of heterodyne systems could also be used.

The processor device 44 may include a memory 45 and a display 47. In fact, the processor device may comprise a typical personal computer. The processor 44 may also be configured to determine the AC and DC components of the amplitudes of the excitation and returned electromagnetic radiation signals. The processor may also be configured to calculate a demodulation factor m. As shown in FIG. 1, the demodulation factor m represents a ratio of the AC component B divided by the DC component A of the returned electromagnetic radiation to the AC component b divided by the DC component a of the excitation electromagnetic radiation. The demodulation factor can be used in conjunction with the phase difference f to more accurately determine characteristics of the target tissue.

If the detector 56 is measuring scattered or reflected electromagnetic radiation, the phase difference and the demodulation factor will provide information about the absorption and reflection characteristics of the target tissue. If the detector 56 is measuring fluorescent radiation emitted by the target tissue, the phase difference and the demodulation factor will provide information about the lifetime and intensity of the fluorescent emissions. In either event, this information can be helpful in determining characteristics of the target tissue. For instance, this information can be used to determine whether a tissue is cancerous or not, the information can be used to distinguish between different types of tissue, and the information can be used to determine chemical properties or the concentrations of various chemicals or ions present in the target tissue.

If the apparatus described above is used to detect fluorescent emissions, the fluorescent emissions can be generated by endogenous or exogenous fluorophores. If the fluorescent material is exogenous, the material may be selected so that it chemically interacts with various compounds in the patient=s body. In this instance, the fluorescent lifetime of the exogenous material would vary depending upon the presence or concentration of a compound or ion. As a result, the phase difference value, and/or the demodulation factor m can be used to determine the presence or concentration of the compound or ion. Examples of exogenous fluorescent materials that would be useful in a method as described above are set forth in U.S. Pat. No. 5,624,847 and U.S. Pat. No. 5,628,310, the contents of each of which are hereby incorporated by reference.

Figure 3:
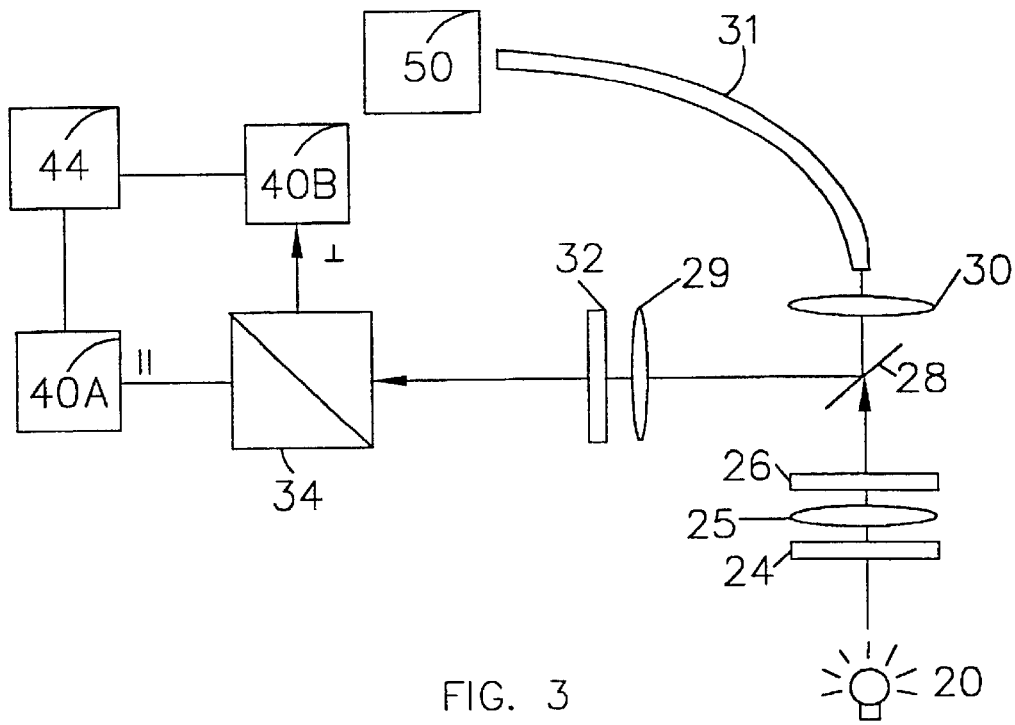
FIG. 3 is a diagram showing an apparatus embodying of the invention capable of performing a polar anisotropy measurement.

A second apparatus and method embodying the invention, which measures fluorescent lifetime via a polarization anisotropy measurement technique, will now be described with reference to FIG. 3. In this measurement technique, a polarized beam of electromagnetic radiation is used to illuminate a target tissue. Components of the fluorophores= excitation dipoles, parallel to the polarization plane of the beam of excitation electromagnetic radiation will then be selectively excited and will emit polarized fluorescent radiation. This emission will have a lifetime that is governed by the physiochemical environment of the fluorophore. Because of Brownian motion, the fluorophores will rotate as they emit radiation. This rotation results in a change in the intensity in each of the emission polarization planes. Brownian rotation in essence provides a time gated window in which to observe the intensity decay due to fluorescence lifetime. By measuring amplitudes of the emitted fluorescent radiation in mutually perpendicular planes, it is possible to determine the lifetime, or decay time, of the fluorescent emissions. This measurement is possible only if the time constant of Brownian rotation, or the rotational correlation time, is not vastly different from the fluorescence lifetime. For most endogenous fluorophores that are indicators of disease this is true. Additionally, exogenous fluorophores can be engineered to satisfy this requirement for applications in disease detection. In a preferred embodiment of the invention, one polarization plane is parallel to the polarization plane of the excitation radiation, and the other is perpendicular to that plane.

This measuring method makes use of the Perrin Equation, which appears below as Equation (6). The Perrin Equation relates fluorescence anisotropy r to the fluorescent lifetime , where $r_0$ is the anisotropy of a molecule in the absence of Brownian motion (the frozen or highly viscous state) and is the rotational (Brownian) correlation time.

$$r_0/r = 1 + t/f \qquad \text{Equation (6)}$$

Strictly speaking, Equation (6) is only valid for a single exponential decay of both fluorescence lifetime and anisotropy. Single exponential anisotropy decay only occurs for a spherical molecule. Also, for simplicity, the rotational correlation time for a sphere is defined according to Equation (7) below, where h is the viscosity, V the volume, R the universal gas constant, and T the absolute temperature.

$$f = (hV)/(RT) \qquad \text{Equation (7)}$$

Using the above equations and assumptions, it is possible to define the anisotropy factor r according to Equation (8), where $I_l$ is the intensity of fluorescent emissions in a plane parallel to the plane of the excitation electromagnetic radiation, and $I_r$ is the intensity of fluorescent emissions in a plane perpendicular to the plane of the excitation electromagnetic radiation.

$$r = (I_1 - I_r)/(I_l + 2I_r) \qquad \text{Equation (8)}$$

An embodiment of the present invention which can measure fluorescent lifetimes, in vivo, by a polarization anisotropy technique will now be described with reference to FIG. 3. In FIG. 3, a source of electromagnetic radiation 20 emits excitation radiation which then passes through a polarizer 24, focusing optics 25, and optionally an emission filter 26. The radiation source 20 can be a laser, a light emitting diode, a fluorescent light tube, an incandescent light bulb, or any other type of light emitting device. In an alternate embodiment, the radiation source 20 and the polarizer 24 could be replaced by a radiation source that emits polarized light.

The polarized and filtered excitation radiation then passes through a dichroic mirror 28, additional focusing optics 30, and one or more optical fibers 31. The polarized excitation radiation exits the optical fibers 31 and illuminates a target tissue 50. Fluorophores in the target tissue 50 will emit fluorescent radiation in response to the excitation electromagnetic radiation. The returned electromagnetic radiation travels back up the optical fiber 31 and through the focusing optics 30. The optical fibers 31 comprise polarization preserving optical fibers such that the polarization of the excitation and return radiation is preserved as the radiation transits the fiber. In other embodiments, one or more emission optical fibers may be used to communicate the excitation radiation to the target tissue 50, and a second group of return optical fibers may be used to communicate the return radiation back to the dichroic mirror 28.

The returned radiation is then reflected by the dichroic mirror 28 through additional optics 29 and, optionally, another filter 32. The returned radiation then enters a polarizing beam splitter 34, which separates the returned electromagnetic radiation into two light beams that are polarized into mutually perpendicular planes. In a preferred embodiment, one polarization plane will be parallel to the polarization plane of the excitation radiation, and the other polarization plane will be perpendicular to that plane. A first one of the separated light beams having a first polarization plane illuminates a first detector 40A. A second of the separated light beams having a second polarization plane that is perpendicular to the first polarization plane illuminates a second detector 40B. The first and second detectors 40A and 40B output signals indicative of the amplitudes of the first and second light beams. The signals from the first and second detectors are then forwarded to a processor 44. The signals from the first and second detectors are used to calculate an anisotropy factor, which provides a measure of the lifetime of the fluorescent emissions. As described above, the fluorescent lifetime can be used to determine various characteristics of the target tissue.

A device or method embodying the present invention, utilizing either the phase shift or the polar anisotropy techniques make it possible to conduct in vivo measurements of tissues on the inside of body passages or lumens. An endoscope embodying the invention can be inserted into a natural body lumen of a patient to search for the presence of cancerous or diseased tissue. This means that no surgery would be required to locate and examine tissues inside the patient=s body.

Either the phase shift or the polar anisotropy method may be used to diagnose disease on the inside surfaces of a body lumen or tissues located immediately below the surface. Since the anisotropy detection method relies on polarized light, a reliable measurement of fluorescence lifetime can be made to a depth of several millimeters before losing resolution due to the depolarizing nature of tissue scattering.

Additionally, the phase shift technique is capable of conducting deep tissue measurements of tissues located several centimeters below the surface of a lumen or organ. This diagnosis is possible by either observing the returned scattered excitation radiation or by observing the scattered fluorescence radiation generated by tissue upon interaction with the scattered excitation radiation. Thus, a device embodying the invention that uses the phase shift technique can determine the presence of cancerous or diseased tissue located below or behind the surface of the body lumen or deep within tissue such as in breast or brain tissue.

The above-described methods could be combined to obtain a better or more accurate measure of target tissue characteristics. For instance, a measurement of the phase shift and demodulation factor of reflected/scattered excitation radiation and a measurement of the phase shift and demodulation factor of a fluorescent emission could be used together to obtain a more accurate determination of target tissue characteristics than one measurement alone. A phase shift and demodulation measurement could also be combined with a polar anisotropy measurement.

Similarly, the phase shift and polar anisotropy techniques could be used in conjunction with known intensity based measurement techniques, as described above in the Background of The Invention, to obtain a better determination of target tissue characteristics.

Examples of methods that combine two or more measurement techniques to arrive at a more accurate ultimate determination are given in U.S. Pat. No. 5,582,168 to Samuels, the contents of which are hereby incorporated by reference.

The techniques described above could also be used to map the conditions of an area of target tissue. For instance, any of the above-described techniques could be used to determine a condition of a target tissue adjacent a distal end of a measuring device. The measuring device could then be moved adjacent a different portion of the target tissue, and the measurements could be repeated. This process could be repeated numerous times to determine the conditions of different portions of a target tissue area. The determined conditions could then be used to create a map of the target tissue area, which could be printed or displayed on a monitor.

One of the most difficult problems with in vivo tissue diagnostics and disease measurement is the biological diversity of normal tissue properties between different patients, or even within the same patient. Furthermore, this diversity is time variant both in the long term and in the short term. Long term variations may be due to patient age, hormonal milieu, metabolism, mucosal viscosity, and circulatory and nervous system differences. Short term variations may be from blood perfusion changes due to heart beat, physical movement, local temperature changes etc.

Because of the variability of tissue characteristics, to accurately determine whether a target tissue is diseased, one needs to compare measurements of the target tissue to measurements of normal tissues from the same patient. The measurements of the known normal tissue should be made concurrently or simultaneously with the measurements of the target tissue. The normal tissue measurements then serve as a baseline for normalcy, variations from which may be interpreted as disease. To arrive at a baseline measurement, a number of strategies can be used.

First, visual characteristics such as pigmentations (nevi) in skin, or polyps in the colon, can be used to identify potentially abnormal regions. Normalized or averaged spectra of multiple regions surrounding these potentially abnormal, visually distinct regions can be used to establish baseline measurements. The baseline measurements can then be compared to measurements taken on the abnormal, visually distinct regions. Measurements of normal and abnormal regions based on visual characteristics could be automated using imaging capabilities of the measurement device itself.

In an alternate strategy, measurements can be taken on spaced apart regions along a portion of a lumen or tissue. The spacing between the regions would be dependent on the type of tissue being diagnosed. Then, differentials between individual measurements taken at different regions would be calculated. If differentials are greater than a preset amount, the tissue between the excessively high differentials would be diagnosed as diseased.

In yet another alternate strategy, a gradient in spectral response as one moves away from a visually suspicious site could also be used as a marker for disease. This is easily automated and can be implemented effectively in any imaging modality.

In addition, pattern recognition algorithms (e.g. neural nets) could also be used to analyze differences in readings taken from various sites in the same patient or from multiple readings from different patients.

Figure 4:
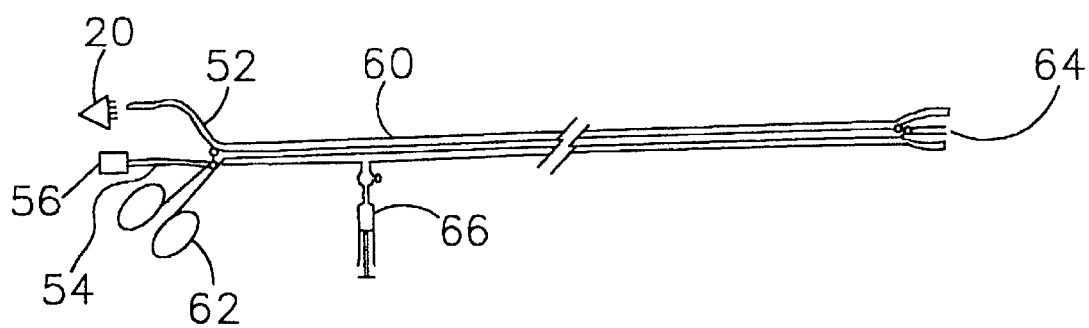
FIG. 4 is a diagram of an endoscope embodying the invention.

FIG. 4 shows an endoscope that could be used to practice any of the above-described measuring techniques. The endoscope 60 includes a transmit optical fiber bundle 52, which can convey excitation electromagnetic radiation from a radiation source 20 to a target tissue. The endoscope 60 also includes a return optical fiber bundle 54 for communicating reflected/scattered electromagnetic radiation or fluorescent emissions from a target tissue to a detector 56. In alternative embodiments, the transmit and return optical fibers could be co-located, or could be the same fibers.

The endoscope 60 may also include a handle 62 for positioning the endoscope, or for operating a device 64 on a distal end of the endoscope 60 intended to remove tissue samples from a patient. The endoscope may also include a device 66 for introducing a dose of medication to a target tissue. Also, the source of electromagnetic radiation 20 may be configured to emit a burst of therapeutic radiation that could be delivered to a target tissue by the endoscope.

FIGS. 5A and 5B show the structure of an endoscope or catheter which may embody the present invention. The apparatus includes a long body portion 70 which is intended to be inserted into a body of the patient. In the case of a catheter, the body portion 70 must have a diameter sufficiently small to be inserted into blood vessels of the patient. In the case of an endoscope, the body portion of the device 70 must have a diameter that is sufficiently small to be inserted into a natural lumen or body cavity of the patient.

The device includes a proximal end 80, which holds proximal ends of optical fibers 72a–72c. The optical fibers extend down the length of the device and terminate at a distal holding portion 74. The distal holding portion 74 holds the optical fibers in a predetermined orientation. The optical fibers are held such that they can illuminate selected portions of the distal end 76 of the device. This orientation also allows the distal end of the optical fibers to receive radiation from selected areas outside the distal end 76 of the device.

As best seen in FIG. 5B, the optical fibers are arranged such that there is a single central optical fiber 72a surrounded by a first ring of optical fibers 72B, which is in turn surrounded by a second ring of optical fibers 72c. Of course, other orientations of the optical fibers are possible.

By applying excitation electromagnetic radiation to selected ones of the optical fibers, and monitoring the returned electromagnetic radiation through selected ones of the optical fibers, is possible to determine characteristics of target tissues at selected locations outside the distal end of the device. For instance, if the central optical fiber 72a emits electromagnetic radiation 90 toward a target tissue, and returned electromagnetic radiation is sensed through the same optical fiber, the returned electromagnetic radiation can be analyzed using any of the above methods to determine characteristics of a target tissue located adjacent the center of the distal end of the device. The same process can be used to determine the condition of a target tissue at different locations around the distal end of the device.

Figure 6A:
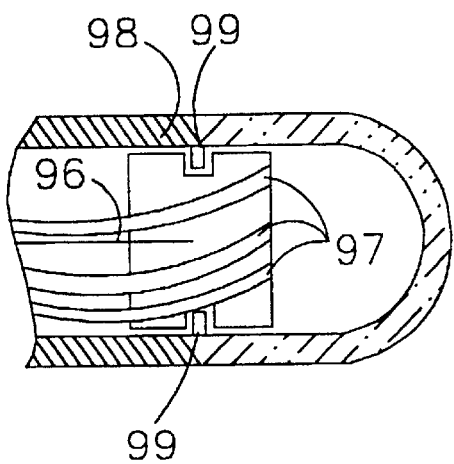
FIGS. 6A, 6B and 6C show the end portions of various embodiments of the invention.
Figure 6B:
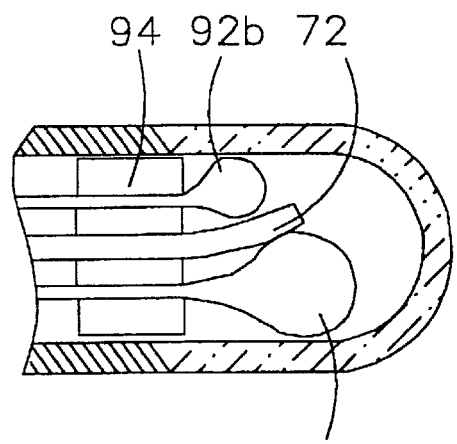
Figure 6C:
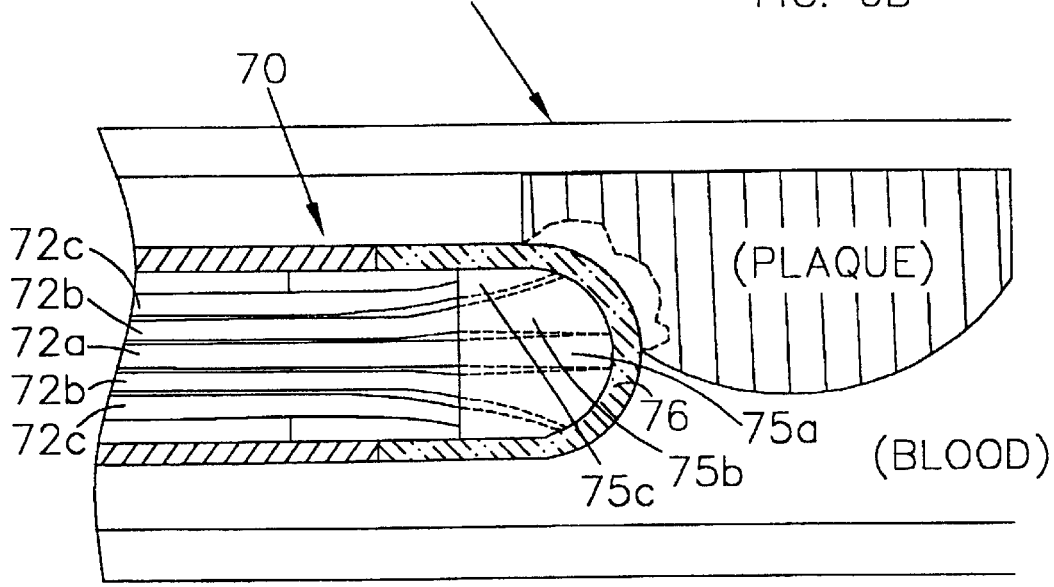

FIGS. 6A–6C show various different distal ends of the device.

In FIG. 6A, the distal ends of the optical fibers are held by a holding portion 98 that aims the distal ends of the optical fibers 97 in a particular direction. A flexible wire or bar 96 is attached to the holding portion 98 and extends to the proximal end of the device. By rotating the flexible wire or bar 96, the holding portion 98 can also be rotated. This allows the distal ends of the optical fibers to be aimed at different portions of the distal end of the device.

FIG. 6B shows another embodiment of the invention that includes one or inflatable balloon portions 92a, 92b. An optical fiber 72 is located in the center of the device by a holding portion 94. Each of the inflatable balloons 92a, 92b is also held by the holding portion 94. By selectively inflating or deflating the different balloon portions, the optical fiber 72 may be aimed to illuminate different portions of the distal end of the device or to receive return radiation from selected locations adjacent the distal end of the device.

FIG. 6C shows an embodiment of the device similar to the embodiment shown in FIGS. 5A and 5B. This figure shows how electromagnetic radiation passing down through the optical fibers 72a–72c can be used to selectively illuminate material or tissue adjacent selected portions of the distal end of the device. In FIG. 6C, only the upper optical fibers are emitting electromagnetic radiation outside the device. This electromagnetic radiation is being used to destroy or atomize plaque which has formed on an inner wall of a blood vessel. By applying electromagnetic radiation to selected ones of the optical fibers, a doctor can carefully remove or correct problems with target tissues or materials.

Figure 7:
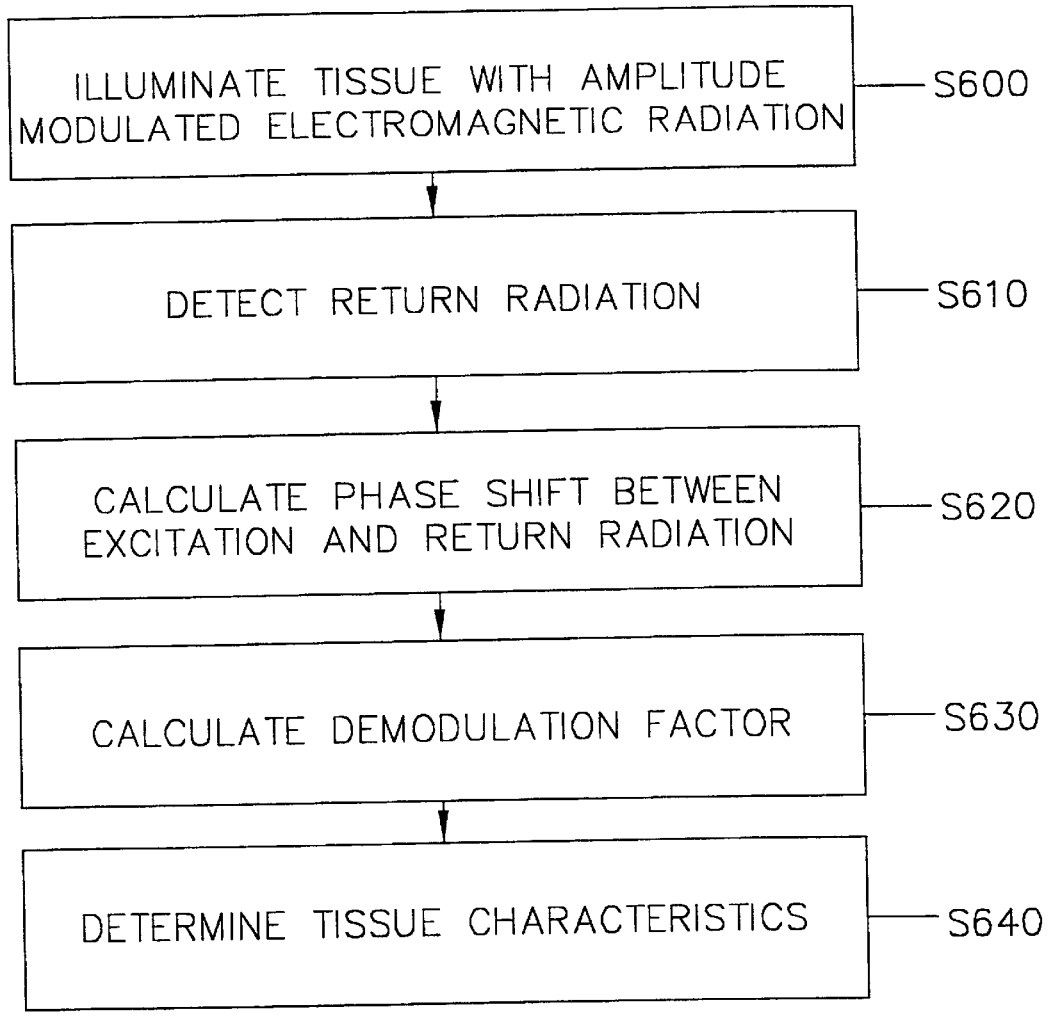
FIG. 7 shows the steps of a method embodying the invention.

FIG. 7 shows steps of a method embodying the invention that can be used to determine the characteristics of a tissue adjacent a device embodying invention. In a first step S600, a target tissue is illuminated with amplitude modulated excitation electromagnetic radiation. In second step S610, returned electromagnetic radiation is detected with a detector. In step S620, a phase shift between the excitation and return electromagnetic radiation is calculated. In another step S630, a demodulation factor representing a ratio of the amplitudes of the excitation and return electromagnetic radiation is calculated. Step S630 is optional but may increase the accuracy of the results. In a final step S640, characteristics of the target tissue are determined based on the calculated phase shift, and optionally the calculated demodulation factor.

Figure 8:
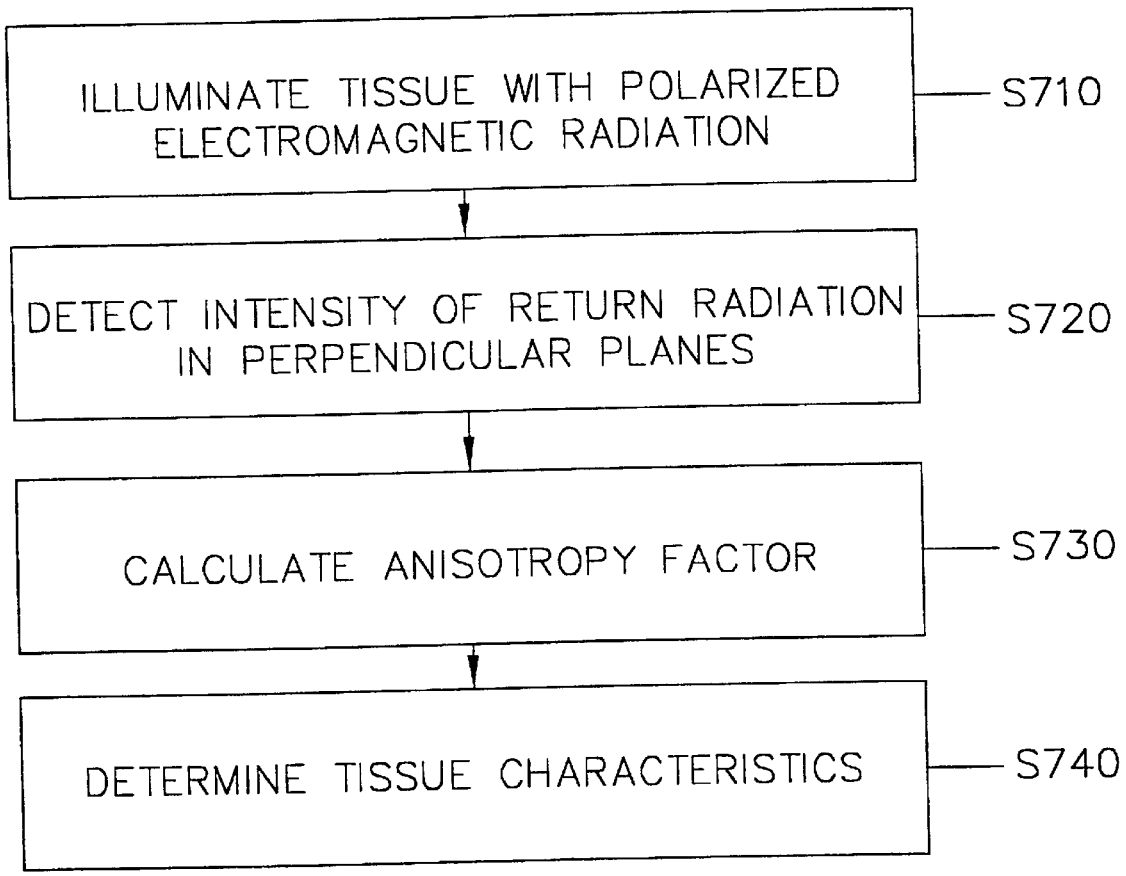
FIG. 8 shows the steps of another method embodying the invention.

FIG. 8 shows another method embodying invention that can be used to determine tissue characteristics. In the first step S710, the target tissue is illuminated with polarized electromagnetic radiation. In the next step S720, the intensity of returned electromagnetic radiation is detected in mutually perpendicular polarization planes. In a preferred embodiment, the amplitude would be detected in planes that are parallel and perpendicular to the polarization plane of the excitation radiation. In the next step S730, an anisotropy factor is calculated based on the detected intensity values for the different polarization planes. In the final step S740, characteristics of a target tissue are determined based on the calculated anisotropy factor.

Figure 9:
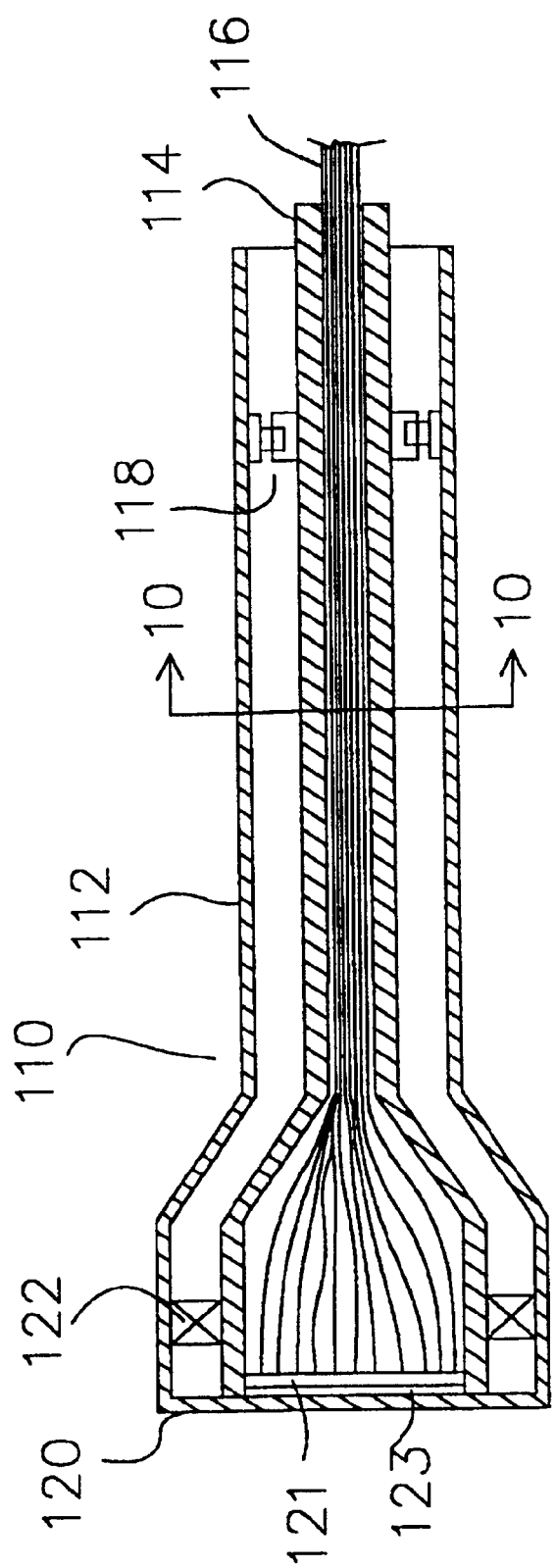
FIG. 9 is a cross-sectional view of a device embodying the invention.

Another device embodying the invention that can be used to determine tissue characteristics is shown, in longitudinal cross-section, in FIG. 9. The instrument 110 includes a cylindrical outer housing 112 with a circular end cap 120 configured to abut the target tissue. A rotating cylindrical inner core 114 is mounted in the outer housing 112. A bundle of optical fibers 116 are located inside the inner core 114.

The optical fibers 116 pass down the length of the inner core 114 and are arranged in a specific pattern at the end adjacent the end cap 120 of the outer housing 112. The end of the inner core 114 adjacent the end cap 120 is mounted within the outer housing 112 with a rotating bearing 122.

The end cap 120 is at least partially transparent or transmissive so that electromagnetic radiation can pass from the optical fibers, through the end cap, to illuminate a target tissue adjacent the end cap 120. Light scattered from or generated by the target tissue would then pass back through the end cap 120 and back down the optical fibers 116.

The inner core 114 is also mounted inside the outer housing 112 by a detent mechanism 118. The detent mechanism is intended to support the inner core 114, and ensure that the inner core is rotatable within the outer housing 112 by predetermined angular amounts.

Figure 10A:
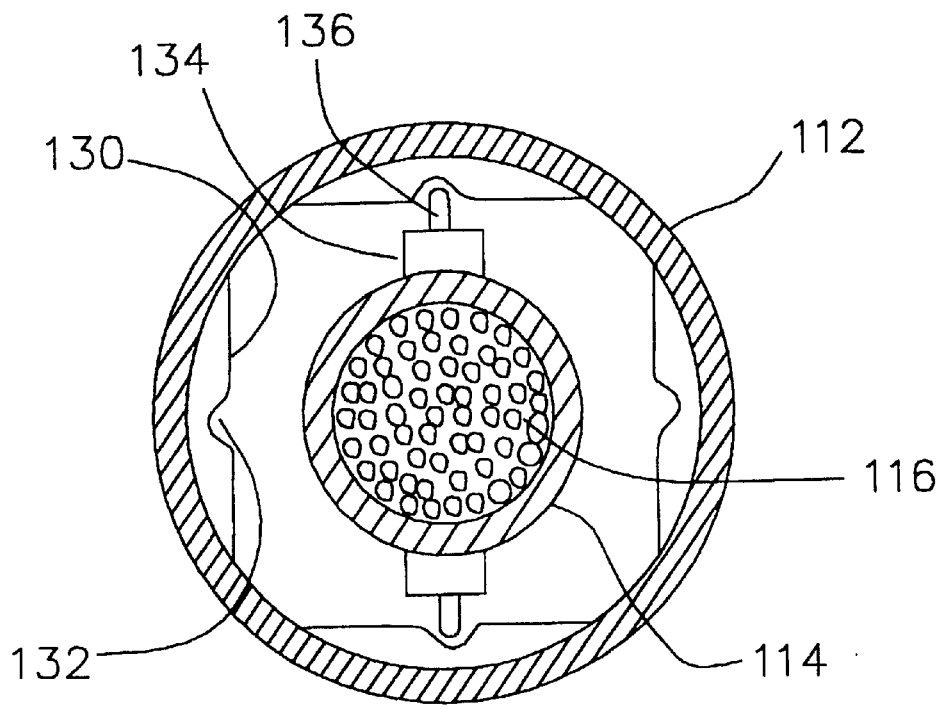
FIGS. 10A and 10B are cross sectional views of the device shown in FIG. 9 taken along section line 10—10.

A cross sectional view of a first embodiment of the instrument, taken along section line 10—10 of FIG. 9, is shown in FIG. 10A. The inner core 114 is supported within the outer housing 112 by the detent mechanism. In this embodiment, the detent mechanism includes two mounts 134 with spring loaded fingers 136 that are biased away from the inner core 114. The detent mechanism also includes four stoppers 130, each of which has a central depression 132. The spring loaded fingers 136 are configured to engage the central depressions 132 of the stoppers 130 to cause the rotatable inner core to come to rest at predetermined angular rotational positions. In the embodiment shown in FIG. 10A, four stoppers are provided in the inner surface of the outer housing 112. Thus, the inner core 114 will be rotatable in increments of 90°. In alternate embodiments similar to the one shown in FIG. 10A, four mounts 134, each having its own spring loaded finger 136, could be attached to the inner core 114. The provision of four such mounts would serve to keep the inner core 114 better centered inside the outer housing 112.

Figure 10B:
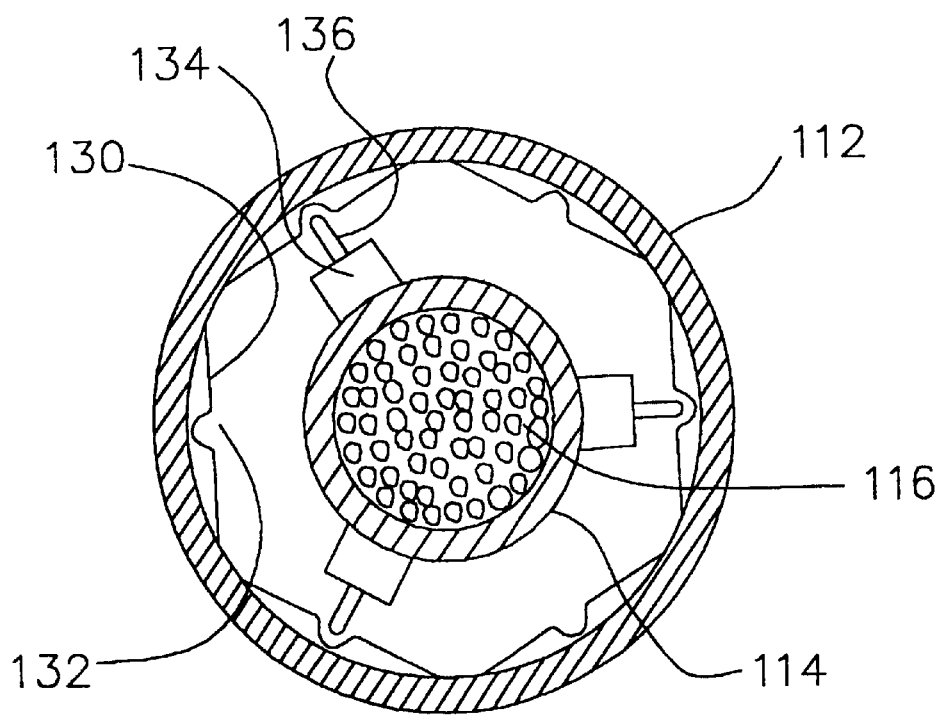

An alternate embodiment of the detent mechanism is shown in FIG. 10B. In this embodiment, six stoppers 130 are spaced around the inside of the outer housing 112. Three mounts 134, each having its own spring loaded finger 136, are mounted on the inner core 114. The three mounts 134 are spaced around the exterior of the inner core 114 approximately 120° apart. This embodiment will allow the inner core to be rotated to predetermined positions in increments of 60°. In addition, the location of the three mounts, 120° apart, helps to keep the inner core 114 supported in the center of the outer housing 112.

The ends of the optical fibers may be mounted on a circular end plate 121 that holds the optical fibers in a predetermined pattern. The circular end plate 121 would be rigidly attached to the end of the cylindrical inner core 114. In addition, an index matching agent 123 may be located between the end plate 121 and the end cap 120 on the outer housing 112. The index matching agent 123 can serve as both an optical index matching agent, and as a lubricant to allow free rotation of the end plate 121 relative to the end cap 120.

Figure 11:
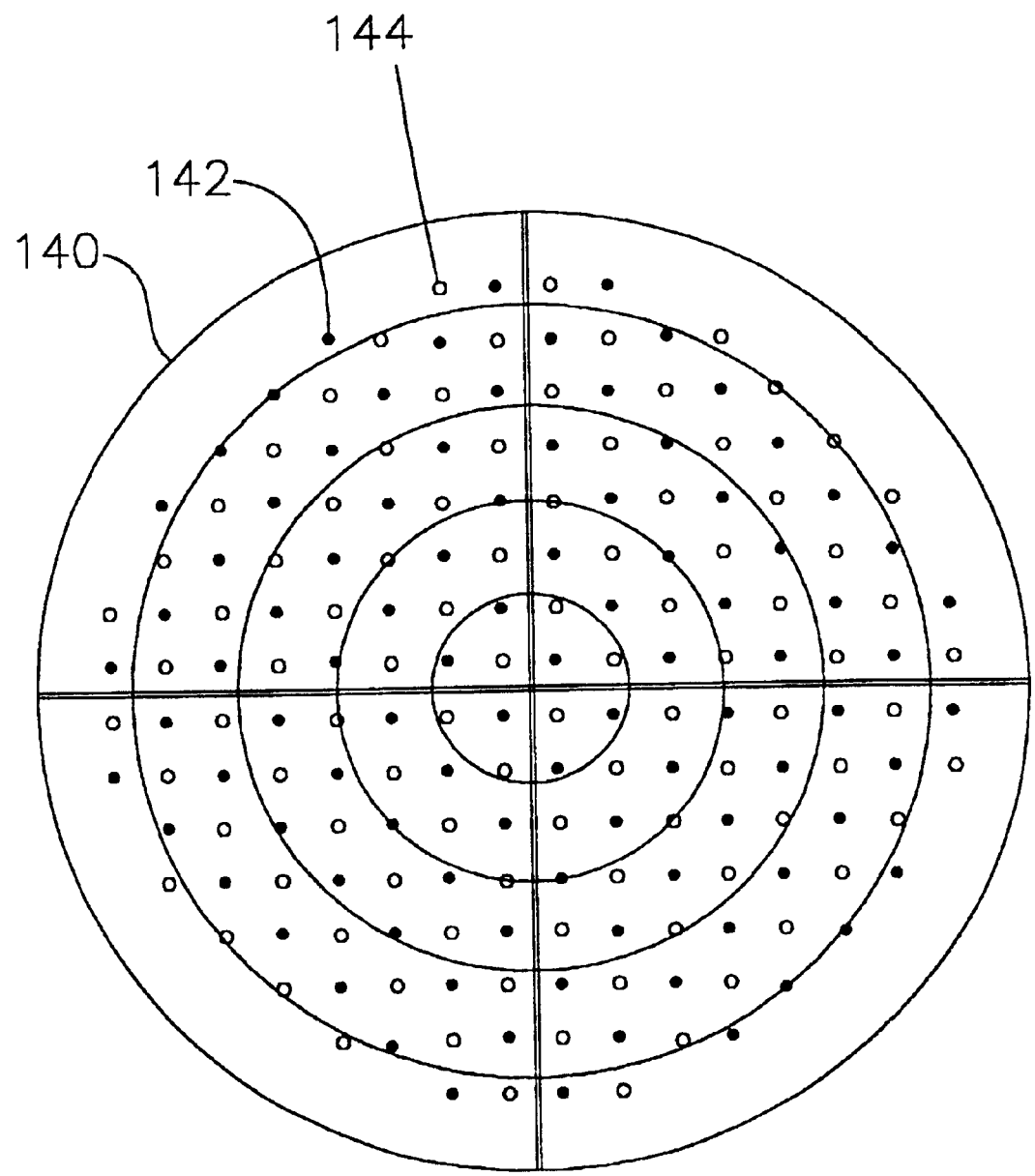
FIG. 11 is a diagram showing the pattern of interrogation points of a device embodying the invention.

A diagram showing how the optical fibers are positioned on the face of an embodiment of the instrument is shown in FIG. 11. The face of the instrument, which would be the end cap 120 of the device shown in FIG. 9, is indicated by reference number 140 in FIG. 11. The black circles 142 represent the locations of optical fibers behind the end cap 120. The hollow circles 144 represent the positions that the optical fibers will move to if the inner core 114 of the instrument is rotated 90°. Thus, each of the circles represent positions that can be interrogated with the optical fibers.

In some embodiments of the device, a single optical fiber will be located at each of the positions shown by the black circles 142 in FIG. 11. In this instance, excitation light would travel down the fiber and be emitted at each interrogation position indicated by a black circle 142. Light scattered from or produced by the target tissue would travel back up the same fibers to a detector or detector array. In alternate embodiments, pairs of optical fibers could be located at each position indicated by a black circle 142. In the alternate embodiments, one optical fiber of each pair would conduct excitation light to the target tissue, and the second optical fiber of each pair would conduct light scattered from or generated by the target tissue to a detector. In still other alternate embodiments, multiple fibers for carrying excitation light and/or multiple fibers for carrying light scattered from or generated by the target tissue could be located at each interrogation position indicated by a black circle 142.

To use an instrument having the optical fiber pattern shown in FIG. 11, the instrument would first be positioned so that the end cap 120 is adjacent the target tissue. The end cap 120 may be in contact with the target tissue, or it might be spaced from the surface of the target tissue. Also, an index matching material may be interposed between the end cap and that target tissue. Then, the optical fibers would be used during a first measurement cycle to simultaneously measure tissue characteristics at each of the interrogation positions in FIG. 11 having a black circle 142. The tissue characteristics could be measured using any of the measurement techniques discussed above. Then, the inner core 114 would be rotated 90° within the outer housing 112, and the optical fibers would be used during a second measurement cycle to simultaneously measure tissue characteristics at each of the interrogation positions in FIG. 11 having a hollow circle 144.

Constructing an instrument as shown in FIGS. 9, 10A or 10B, and having the optical fiber pattern shown in FIG. 11, has several important advantages. First, constructing an instrument in this manner allows the instrument to interrogate many more points in the target tissue than would have been possible if the inner core did not rotate. The ability to rotate the inner core 114, and take a second series of measurements at different locations on the target tissue, essentially increases the resolution of the device.

In addition, when a large number of optical fibers are packed into the tissue contacting face of an instrument, cross-talk between the optical fibers can occur. The cross-talk can occur when excitation light from one interrogation position scatters from the target tissue and enters an adjacent interrogation position. Cross-talk can also occur if excitation light from a first interrogation position travels through the target tissue and enters an adjacent interrogation position. One of the easiest ways to reduce or eliminate cross-talk is to space the interrogation positions farther apart. However, increasing the spacing between interrogation positions will reduce the resolution of the device.

An instrument embodying the present invention, with a rotatable inner core, allows the interrogation positions to be spaced far enough apart to reduce or substantially eliminate cross-talk, while still obtaining excellent resolution. Thus, good resolution is obtained without the negative impact to sensitivity or selectivity caused by cross-talk. In addition, fewer optical fibers and fewer corresponding detectors are required to obtain a given resolution.

In addition, the ability to obtain a plurality of tissue measurements simultaneously from positions spaced across the entire target tissue has other benefits. If the instrument is intended to detect cancerous growths or other tissue maladies, the target tissue area interrogated by the instrument is likely to have both normal tissue, and diseased tissue. As noted above, tissue characteristics can vary significantly from person to person, and the tissue characteristics can vary significantly over relatively short periods of time. For these reasons, the most effective way to determine the locations of diseased areas is to establish a baseline for normal tissue, then compare the measurement results for each interrogation point to the baseline measurement. In other words, the easiest way to determine the location of a diseased area is to simply look for a measurement aberration or variance.

Because tissue characteristics can change relatively quickly, in order to establish accurate, clearly defined variances between tissue characteristics, it is desirable to take a plurality of readings simultaneously over as large an area as possible. Ideally, all measurements should be conducted during the same time period. Because tissue tumors can be as small as approximately 1 mm, the resolution of the device is preferably 1 mm. In other words, to obtain the requisite resolution, the spacing between interrogation positions should be 1 mm. Unfortunately, when the interrogation positions are 1 mm apart, significant cross-talk can occur, and the accuracy of the measurement results is poor.

An instrument embodying the present invention allows the interrogation positions to be spaced sufficiently far apart to essentially eliminate cross-talk, while still obtaining the requisite 1 mm resolution. Although not all measurements are obtained at exactly the same time, during each measurement cycle, simultaneous measurements are made at positions spaced across the entire target tissue, which should include both normal and diseased areas. Thus, the results from each measurement cycle can be used to detect variances in tissue characteristics that help to localize diseased areas. For these reasons, an instrument embodying the present invention balances the competing design requirements of resolution, elimination of cross-talk, and the desire to make all measurements simultaneously to ensure that time-varying tissue characteristics are taken into account.

Figure 12:
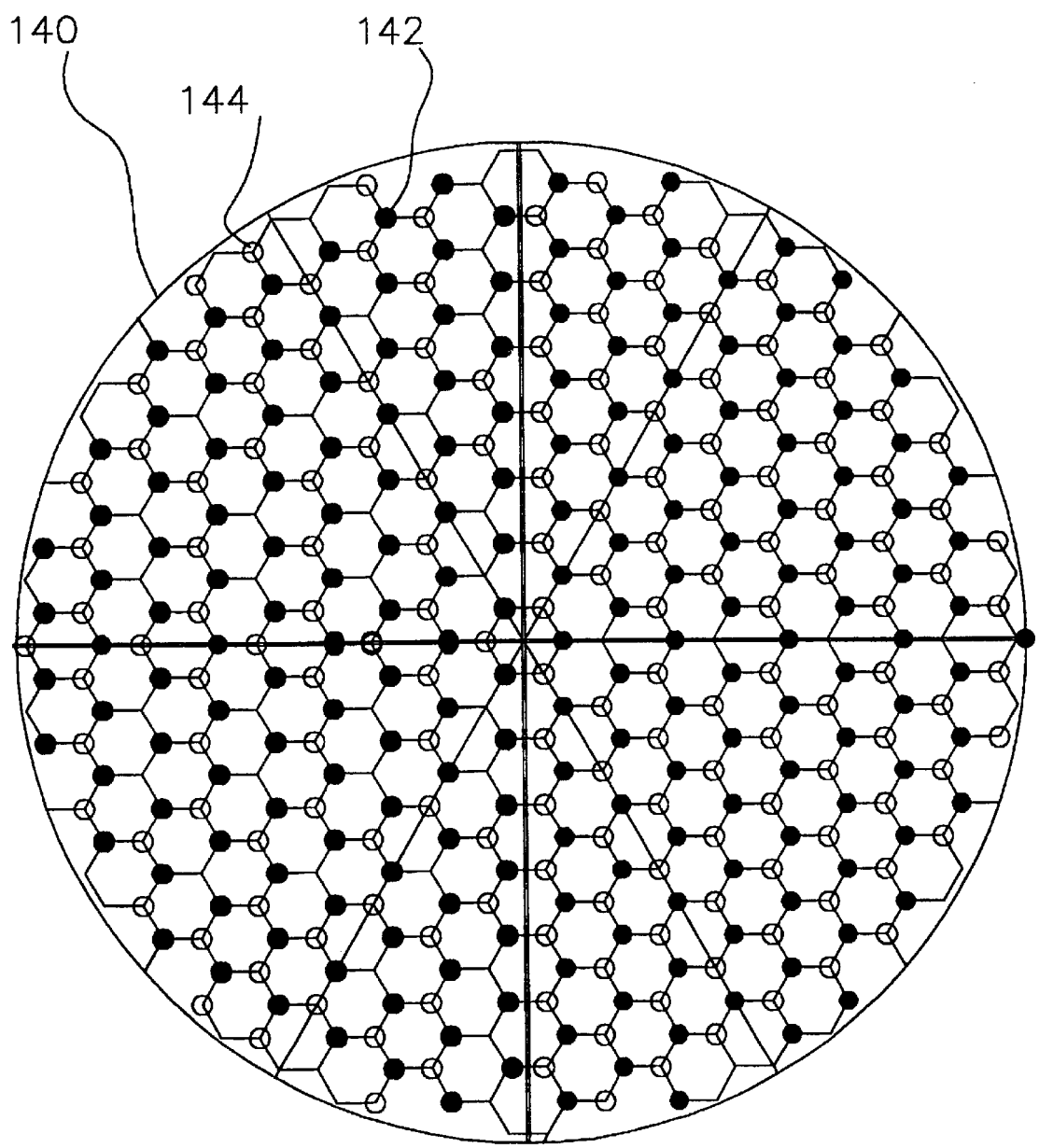
FIG. 12 is another diagram showing the pattern of interrogation points of a device embodying the invention.

A second arrangement for the optical fibers of a device as shown in FIG. 9 is depicted in FIG. 12. In this embodiment, the interrogation positions are arranged in a hexagonal honeycomb pattern. The black circles 142 indicate the positions that would be occupied by optical fibers during a first measurement cycle, and the hollow circles 144 indicate positions that would be occupied by the optical fibers during a second measurement cycle after the inner core 112 has been rotated by 60°. This pattern achieves maximum spacing between adjacent interrogation positions during each measurement cycle, and essentially doubles the resolution of the instrument.

Figure 13:
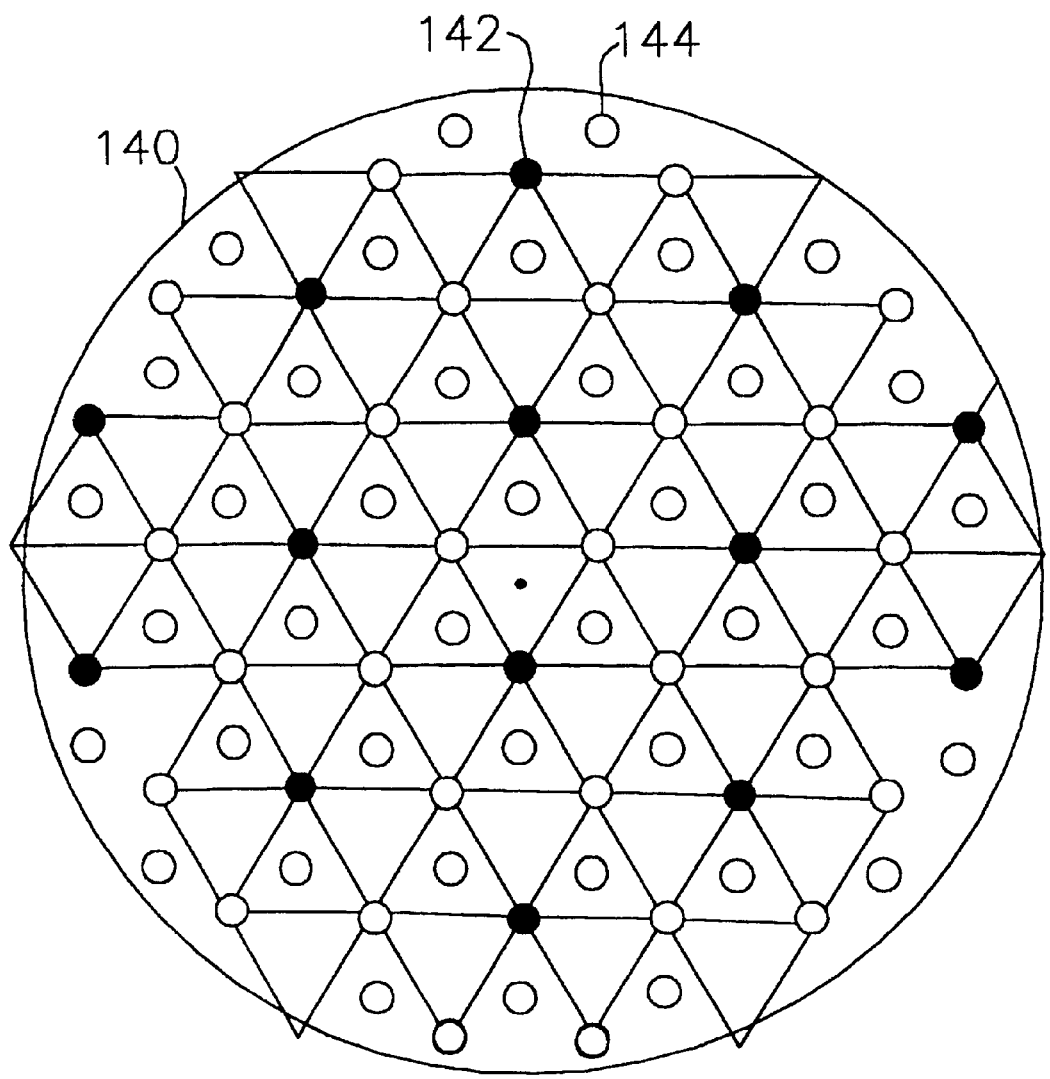
FIG. 13 is yet another diagram showing the pattern of interrogation points of a device embodying the invention.

A third arrangement for the optical fibers of a device shown in FIG. 9 is depicted in FIG. 13. In this embodiment, the optical fibers are again arranged according to a hexagonal honeycomb pattern. However, far fewer optical fibers are used in this embodiment. This third embodiment is intended for use in a measurement process that calls for six measurement cycles. The inner core of the device would be rotated 60° between each measurement cycle. Over the course of the six measurement cycles, the device would ultimately interrogate all the black circled 142 and hollow circled 144 interrogation positions shown in FIG. 13. This embodiment allows for even greater separation distances between interrogation positions (to reduce or substantially eliminate cross-talk) while still achieving excellent measurement resolution. In addition, far fewer optical fibers and corresponding detectors would be required to achieve a given measurement resolution.

Experimental studies were conducted by the applicants to determine the spacing between interrogation positions that is needed to substantially eliminate cross-talk. The studies were conducted using a pair of optical fibers at each interrogation position, wherein one fiber in each pair provides excitation light, and the other fiber in each pair is used to detect light. The excitation optical fibers had a diameter of 200 mm, and the detection fibers had a diameter of 100 mm. Measurements were made on optical reference standards, and tissue. Under these conditions, it was necessary to space the interrogation positions approximately 3 mm apart to substantially eliminate cross-talk. Thus, if an instrument were not designed as described above, so that the inner core can rotate the interrogation positions to different locations on the target tissue, the device would only be capable of achieving a resolution of 3 mm.

The presently preferred embodiment of the invention utilizes an optical fiber pattern similar to the one shown in FIG. 13. Thus, the device is designed to conduct six measurement cycles to complete all measurements within the target tissue. The inner core 114 is rotated 60° between each measurement cycle. The presently preferred embodiment utilizes optical fiber pairs at each interrogation position. Each optical fiber pair includes an excitation fiber having a 200 mm diameter, and a detection optical fiber having a 100 mm diameter. The arrangement of the optical fibers allows the interrogation positions to be spaced approximately 3.0–3.5 mm apart, while still achieving a resolution of approximately 1 mm.

Figure 14:
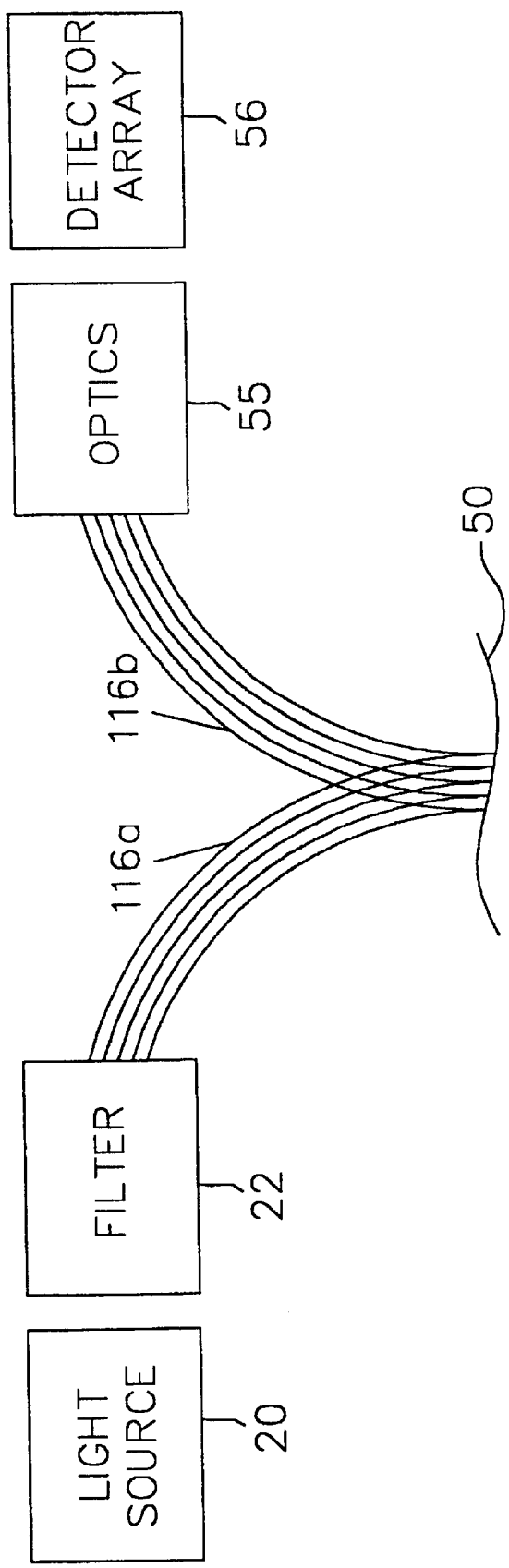
FIG. 14 is a block diagram of a device embodying the invention.

To determined the locations of diseased areas within a target tissue it is necessary to take measurements at a plurality of different locations in the target tissue spaced in at least two dimensions. Each measurement may require multiple excitation wavelengths, and detection of multiple wavelengths of scattered or generated light. Thus, the measurements involve three measurement dimensions, two dimensions for the area of the target tissue, and a third dimension comprising the spectral information. A device capable of conducting measurements in these three dimensions is shown in FIG. 14.

The instrument includes a light source 20, and a filter assembly 22. A plurality of excitation optical fibers 116a lead from the filter assembly 22 to the target tissue 50. A plurality of detection fibers 116b lead away from the target tissue 50. The excitation optical fibers 116a and the detection optical fibers 116b are arranged in pairs as described above.

The light source 20 and filter assembly 22 allow specific wavelengths of light to be used to illuminate the target tissue 50 via the excitation optical fibers 116a. The filter assembly 22 could be a single band pass optical filter, or multiple optical filters that can be selectively placed between the light source 20 and the excitation optical fibers 116a. Alternatively, the light source 20 and filter assembly 22 could be replaced with a wavelength tunable light source. In yet other alternate embodiments, a plurality of light sources, such as lasers, could be used to selectively output specific wavelengths or wavelength bands of excitation light.

The detection fibers lead to an optical system 55. The light from the detection fibers 116b passes through the optical system and into a detector array 56. The detector array may comprise a plurality of photosensitive detectors, or a plurality of spectrophotometers. The detector array 56 is preferably able to obtain measurement results for each of the detection fibers 116b simultaneously.

The optical system 55 can include a plurality of optical filters that allow the detector array to determine the intensity of light at certain predetermined wavelengths. In a preferred embodiment, the detector array would be a two dimensional array of photosensitive detectors, such as a charge coupled device (CCD). The optical system would comprise a spectrograph that is configured to separate the light from each detection optical fiber 116b into a plurality of different wavelengths, and to focus the different wavelengths across a line of pixels on the CCD. Thus, each line of pixels on the CCD would correspond to a single detection fiber. The intensities of the different wavelengths of light carried by a single detection fiber 116b could be determined based on the outputs of a line pixels of the CCD. The greater the output of a particular pixel, the greater the intensity at a particular wavelength.

The preferred embodiment is able to achieve excellent flexibility. Because all wavelengths of light are always detected, the instrument software can simply select the pixels of interest for each measurement, and thereby determine the intensity at particular wavelengths. During a first measurement, certain pixels representative of scattering characteristics could be examined. During a subsequent measurement, different pixels representative of fluorescent characteristics could be examined. Also, the device could be essentially re-configured to take completely different measurements by simply changing the control software. Thus, a single device could be used for a wide variety of different kinds of measurements.

In preferred methods of the present invention, one of the structures described above would be used to conduct a series of measurements cycles, and the inner core of the device would be rotated between measurement cycles. In the preferred methods, however, two or more measurements may be conducted during each measurement cycle. For instance, during a single measurement cycle the device may conduct a measurement of scattering characteristics, and a measurement of fluorescent characteristics. Once all measurement of a measurement cycle are completed, the inner core would be rotated, and additional measurement cycles would be conducted.

In each of the embodiments described immediately above, a plurality of measurement cycles are conducted on a target tissue, and an inner core having optical fibers arranged in a predetermined pattern is rotated between measurement cycles. Although the presently preferred embodiments utilize rotating devices to accomplish a plurality of measurements on a target tissue, alternate embodiments could use some other movement mechanism other than a rotating one. The invention encompasses other types of movement or translational devices that allow a plurality of measurements to be taken on a target tissue with a limited number of detectors that are spaced far enough apart to avoid cross-talk.

The foregoing embodiments are merely exemplary and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art.

What is claimed is:

1. An instrument for determining characteristics of a target material, comprising:
   an outer housing;
   an inner core that is rotatably mounted within the outer housing;
   a plurality of interrogation devices comprising a plurality of optical fibers mounted on the inner core in a predetermined pattern; and
   a detent mechanism attached to the inner core, wherein the detent mechanism is configured to allow the inner core to be rotated between a plurality of predetermined rotational positions relative to the outer housing.

2. The instrument of claim 1, wherein the plurality of interrogation devices are mounted on the inner core so that when the inner core is positioned at a first predetermined rotational position, the interrogation devices are positioned adjacent a first plurality interrogation positions relative to the outer housing, and wherein rotation of the inner core from the first predetermined rotational position to a second predetermined rotational position causes the plurality of interrogation devices to be repositioned adjacent a second plurality of interrogation positions.

3. The instrument of claim 2, wherein the instrument is configured such that the plurality of interrogation devices are repositioned to a plurality of predetermined interrogation positions each time the inner core is rotated to a corresponding predetermined rotational position.

4. The instrument of claim 3, wherein none of the predetermined interrogation positions are coincident.

5. The instrument of claim 1, wherein the predetermined pattern in which the plurality of interrogation devices are mounted on the inner core minimizes cross-talk between adjacent interrogation devices.

6. The instrument of claim 1, wherein sensing portions of the plurality of interrogation devices are mounted on a face of the inner core, and wherein the predetermined pattern in which the plurality of interrogation devices are mounted on the inner core distributes the plurality of interrogation devices substantially evenly across the face of the inner core.

7. The instrument of claim 1, wherein at least two optical fibers are located at each interrogation position, wherein at least one optical fiber at each interrogation position is configured to conduct excitation light to the interrogation position, and wherein at least one optical fiber at each interrogation position is configured to receive light that is scattered from or generated by a target material.

8. The instrument of claim 1, further comprising a detector array, wherein light scattered from or generated by a target material is conducted to the detector array by at least some of the optical fibers.

9. The instrument of claim 1, wherein the detent mechanism is configured to support at least a portion of the inner core inside the outer housing.

10. The instrument of claim 1, wherein the outer housing includes an end cap, and wherein the plurality of interrogation devices are configured to project excitation light through the end cap and to detect light from a target material that passes through the end cap.

11. The instrument of claim 10, wherein an index matching agent is located between the end cap and the plurality of interrogation devices.

12. The instrument of claim 11, wherein the index matching agent also acts as a lubricant to allow the inner core to rotate freely within the outer housing.

13. An instrument for determining characteristics of a target material, comprising:
   an outer housing;
   an inner core that is rotatably mounted within the outer housing;
   a plurality of interrogation devices mounted on the inner core in a predetermined pattern; and
   a detent mechanism attached to the inner core, wherein the detent mechanism is configured to allow the inner core to be rotated between a plurality of predetermined rotational positions relative to the outer housing, and wherein stops are formed on an inner surface of the outer housing, and wherein the detent mechanism comprises at least one detent mount that is attached to the inner core and that is configured to interact with the stops to hold the inner core in the plurality of predetermined rotational positions.

14. The instrument of claim 13, wherein each stop includes a depression, wherein each at least one detent mount includes a biased member, and wherein each biased member is configured to nest in a depression of a stop to hold the inner core in one of the plurality of predetermined rotational positions.

15. An instrument for determining characteristics of a target material, comprising:

an outer housing;

means for determining characteristics of a target material at a plurality of predetermined interrogation locations arranged in a predetermined pattern, the means for determining comprising a plurality of optical fibers; and means for holding the determining means in a plurality of predetermined positions relative to the outer housing, the holding means comprising means for rotating the determining means about an axis.

16. The instrument of claim 15, wherein the device is configured such that moving the determining means between the plurality of predetermined positions allows the determining means to determine characteristics of a target material at a plurality of interrogations locations, and wherein none of the interrogation locations are coincident.

17. The instrument of claim 15, wherein the predetermined pattern minimizes cross-talk between adjacent interrogation locations.

18. The instrument of claim 15, wherein the outer housing includes an end cap, and wherein the interrogation locations are substantially evenly distributed across the end cap.

19. A method of detecting characteristics of a target material, comprising the steps of:

positioning a plurality of interrogation devices comprising a plurality of optical fibers that are arranged in a pattern adjacent a first plurality of interrogation positions on a target material;

detecting characteristics of the target material at the first plurality of interrogation positions;

repositioning the plurality of interrogation devices so that they are adjacent at least one additional plurality of interrogation positions on the target material, wherein the first and at least one additional plurality of positions are not coincident; and detecting characteristics of the target material at the at least one additional plurality of interrogation positions, wherein the repositioning step comprises rotating the plurality of interrogation devices around a common axis.

20. The method of claim 19, wherein each detecting step comprises the steps of:

detecting a first type of characteristics of the target material at a plurality of interrogation positions; and detecting a second type of characteristics of the target material at a plurality of interrogation positions.

21. A method of detecting characteristics of a target material, comprising the steps of:

positioning a plurality of interrogation devices that are arranged in a pattern adjacent a first plurality of interrogation positions on a target material;

detecting characteristics of the target material at the first plurality of interrogation positions;

repositioning the plurality of interrogation devices so that they are adjacent at least one additional plurality of interrogation positions on the target material, wherein the first and at least one additional plurality of interrogation positions are not coincident; and detecting characteristics of the target material at the at least one additional plurality of interrogation positions, wherein the first type of characteristics comprise scattering characteristics, and wherein the second type of characteristics comprise fluorescent characteristics.

* * * * *